(12) United States Patent
Fleischer et al.

(10) Patent No.: US 12,349,875 B2
(45) Date of Patent: Jul. 8, 2025

(54) DEVICE FOR COLLECTING MIDSTREAM URINE FROM A HUMAN INDIVIDUAL

(71) Applicant: Aarhus Medical ApS, Risskov (DK)

(72) Inventors: Jesper Fleischer, Højberg (DK); Peter Christian Boldsen, Risskov (DK); Anders Geert Jensen, Risskov (DK); Morten Haaning Charles, Risskov (DK)

(*) Notice: Subject to any disclaimer, the term of this patent is extended or adjusted under 35 U.S.C. 154(b) by 943 days.

(21) Appl. No.: 17/059,653

(22) PCT Filed: Jun. 18, 2019

(86) PCT No.: PCT/DK2019/050195
§ 371 (c)(1),
(2) Date: Nov. 30, 2020

(87) PCT Pub. No.: WO2019/242823
PCT Pub. Date: Dec. 26, 2019

(65) Prior Publication Data
US 2021/0204916 A1    Jul. 8, 2021

(30) Foreign Application Priority Data

Jun. 18, 2018 (DK) .......................... PA 2018 00283

(51) Int. Cl.
*A61B 10/00* (2006.01)
*A61B 90/98* (2016.01)
*B01L 3/00* (2006.01)

(52) U.S. Cl.
CPC .......... *A61B 10/007* (2013.01); *A61B 90/98* (2016.02); *B01L 3/502* (2013.01);
(Continued)

(58) Field of Classification Search
CPC ......... A61B 10/007; A61B 90/98; A61B 5/20; A61B 10/00; B01L 3/502;
(Continued)

(56) References Cited

U.S. PATENT DOCUMENTS 4,557,274 A * 12/1985 Cawood .............. A61B 10/007
600/580
5,813,973 A * 9/1998 Gloth ............... A61B 17/12022
600/29
(Continued)

FOREIGN PATENT DOCUMENTS

CA    2170936 A    9/1996
CN    107981890 A    5/2018
(Continued)

OTHER PUBLICATIONS

International Search Report issued in PCT/DK2019/050195 on Oct. 17, 2019.
Danish Search Report issued in PA 2018 00283 on Nov. 21, 2018.

*Primary Examiner* — Nicholas J. Weiss
*Assistant Examiner* — Gabriella E Burnette
(74) *Attorney, Agent, or Firm* — Krishna Kalidindi

(57) ABSTRACT

The invention relates to a urine collection device (100) for collecting midstream urine; wherein said device, in the orientation intended during urine collection, comprising: a first recipient (2) for urine; a second recipient (4) for urine; a urine diverting means (5); wherein said urine collection device (100) comprises a third recipient (14) for urine, wherein said third recipient for urine comprises an evacuated container; or wherein said third recipient (14) for urine comprises a container which is configured for becoming evacuated by being in fluid connection with a vacuum pump; wherein said urine collection device comprises a conduit (16) having an opening (18) in a first end (20) and an opening (22) in a second end (24) thereof; wherein said first
(Continued)

end (20) of said conduit (16) is arranged at the interior of said second recipient (4) for urine; wherein said opening (22) in said second end (24) of said conduit (16) is in fluid connection with the interior of said third recipient (14) for urine; wherein said opening of said first end (20) of said conduit 16 comprises a moist soluble plug (26), thereby blocking access through said conduit between said second recipient (4) for urine and said third recipient (14) for urine until dissolution of said plug.

20 Claims, 11 Drawing Sheets

(52) U.S. Cl.
CPC ..... *B01L 2300/046* (2013.01); *B01L 2300/12* (2013.01); *B01L 2400/0622* (2013.01); *B01L 2400/0677* (2013.01)

(58) Field of Classification Search
CPC ........... B01L 2300/046; B01L 2300/12; B01L 2400/0622; B01L 2400/0677; B01L 3/00; A61F 5/44; A61G 9/00; A61G 7/00
See application file for complete search history.

(56) References Cited

U.S. PATENT DOCUMENTS

| | | | |
|---|---|---|---|
| 6,409,971 B1* | 6/2002 | Wilkinson | B01L 3/50825 422/537 |
| 10,335,121 B2* | 7/2019 | Desai | A61B 10/007 |
| 2003/0164051 A1 | 9/2003 | Kunimune | |
| 2008/0056962 A1* | 3/2008 | Mulqueen | A61B 5/150389 422/130 |
| 2014/0371628 A1* | 12/2014 | Desai | A61F 5/455 600/574 |
| 2015/0320583 A1* | 11/2015 | Harvie | A61F 5/441 604/351 |
| 2018/0214297 A1* | 8/2018 | Hughett | A61B 5/208 |

FOREIGN PATENT DOCUMENTS

| | | |
|---|---|---|
| GB | 2162312 A | 1/1986 |
| WO | 2008/065325 A | 6/2008 |
| WO | 2008/094771 A | 8/2008 |
| WO | 2014/120133 A | 8/2014 |

* cited by examiner

DEVICE FOR COLLECTING MIDSTREAM URINE FROM A HUMAN INDIVIDUAL

FIELD OF THE INVENTION

The present invention relates in general to the field of medical equipment. More specifically the present invention relates in a first aspect to a urine collection device for collecting midstream urine. In a second aspect the present invention relates to a wearable device comprising a urine collection device according to the first aspect. In a third aspect the present invention relates to the use of a urine collection device according to the first aspect of the present invention or of a wearable device according to the second aspect of the present invention for collecting a midstream portion of urine from a human individual.

BACKGROUND OF THE INVENTION

Within the field of medicine, it is customary to collect samples from a human body in order to examine such samples with the aim to deduct a diagnosis relating to various conditions of the individual, from which the sample has been collected.

Such samples to be collected may relate to tissue or bodily fluids.

Collecting and examining urine from an individual may accordingly form the basis for an essential examination to diagnose a potential bacterial infection in the urinary tract.

Examples of inflammations in the urinary track and examples of other medical conditions which may be diagnosed from urine are: general infections, bladder infections, autoimmune diseases, bladder cancer, kidney functions, pregnancy, diabetes 1, diabetes 2, internal bleedings, poisonings and prostata.

However, as the urethra is prone to contain bacteria originating from its opening's exposure to the surroundings, a mere uncritically collection of urine and a subsequent diagnosis conducted on such urine may lead to false positive results in relation to identification of bacterial infections in the individual from which the urine has been collected.

For this reason, when conducting a diagnosis on the basis of urine from an individual, it must be assured that the collected urine, which is subjected to the diagnosis, is not forestream urine which may be prone to contain bacteria which have an external origin; rather, it must be assured that the collected urine is so-called "midstream urine", which is defined as urine not belonging to the first portion of urine situated in the urethra and being emptied by the individual.

It is a generally accepted definition that midstream urine is that portion of urine, being emptied from a human individual, which does not belong to the first 10 milliliters of expelled urine.

Whereas healthy adult persons without any assistance, except receiving instructions, will be able to urinate into a urine collection recipient in such a way that only a midstream portion of urine is collected, there are groups of persons in respect of whom the situation is different.

Examples of such group of persons are disabled persons, weak or diseased persons, small children, persons with reduced motility control and persons with reduced bladder control.

In respect of collecting a midstream urine, devices have been provided which are able to collect both a forestream and a midstream portion of urine and wherein the device provides for automatically separating the midstream portion from the forestream portion of urine.

One such device is disclosed in WO 2008/094771 A1. This document discloses a device and a method for collecting a midstream urine. The device comprises a tube through which urine is being led. A lower part of the tube comprises a through-going hole which is covered with a water soluble cover. Once urine is being led into the tube, a first portion of urine will pass the whole tube. Having been exposed for urine for a short period of time, the water soluble cover will eventually dissolve and urine will subsequently be directed from the tube, through the through-going hole in the tube and into a collector arranged below the through-going hole. In this way, the collection of only midstream urine is assured.

Another example of a device for collecting a midstream portion of urine is disclosed in US 2005/02400164 A1. This document discloses a disposable device for collecting a midstream portion of urine, especially intended to be worn by small children.

The device disclosed in US 2005/02400164 A1 comprises a collection bag for urine. The collection bag comprises an opening which is provided with a delaying mechanism. An absorbent material is provided on the bag in such a way that this absorbing material surrounds the opening. The delaying mechanism may comprise a cover covering the opening which cover is being made from a urine dissolving material. The working mode of the device US 2005/02400164 A1 is as follows: a first stream of urine being led to the outside of the collection bag in the area above the cover of the opening will be directed to the absorbing material surrounding the opening and will be absorbed by this absorbing material. Once being exposed to urine, the delaying mechanism will after a short while provide for access to the interior of the bag. Thereby the midstream portion of urine will be collected in the bag.

Although devices have been developed which provide for separating and collection of a midstream portion of urine from a forestream portion of urine, these devices nevertheless presents a number of disadvantages.

One of these disadvantages is that once a midstream portion of urine has been collected by these devices, this portion of midstream urine need be handled and transferred to a proper vial in which the urine can be stored until the process of conducting the analysis leading to a diagnosis.

Such handling necessitates human involvement and hence represents labor time needed in respect of nurses or assistants, inconvenience and potential delays.

Moreover, human handling of urine samples collected by the prior art devices involves the risk of exposing the urine samples for bacteria of external origin, thus representing a risk of obtaining false positive diagnosis results.

A further disadvantage of the prior art devices is that they do not represent a satisfactorily solution for persons suffering from lack of bladder control and therefore must use diapers.

It is an objective of the present invention to provide devises and uses which overcome the disadvantages of the prior art devices.

BRIEF DESCRIPTION OF THE INVENTION

These objectives are fulfilled according to the first, the second and the third aspect of the present invention.

Accordingly, the first aspect of the present invention relates to a urine collection device for collecting midstream urine; wherein said device, in the orientation intended during urine collection, comprising:

a first recipient for urine;
a second recipient for urine;
a urine diverting means;
characterized in that said urine collection device comprises a third recipient for urine, wherein said third recipient for urine comprises an evacuated container; or wherein said third recipient for urine comprises a container which is configured for becoming evacuated by being in fluid connection with a vacuum pump;
wherein said urine collection device comprises a conduit having an opening in a first end and an opening in a second end thereof;
wherein said first end of said conduit is arranged at the interior of said second recipient for urine;
wherein said opening in said second end of said conduit is in fluid connection with the interior of said third recipient for urine;
wherein said opening of said first end of said conduit comprises a moist soluble plug, thereby blocking access through said conduit between said second recipient for urine and said third recipient for urine, until dissolution of said plug.

In a second aspect, the present invention relates to a wearable device for collecting urine from a human individual, wherein said wearable device comprises a urine collecting device according to the first aspect of the present invention; wherein said wearable device comprises a material having an inner surface configured to face at least a lower portion of the pelvic region of a human individual, and an outer surface arranged opposite to the inner surface.

In a third aspect the present invention relates to a use of the urine collection device according to the first aspect of the present invention, or of a wearable device according to the second aspect of the present invention for collecting a midstream urine from a human individual.

The present invention in its various aspects provides for an improved urine collection device and an improved wearable device for separating a midstream portion from a forestream portion of urine and for collecting such midstream portion of urine in an easy and convenient way among human individuals with no clear bladder control, which moreover reduces the risk of contamination of the collected midstream urine with bacteria of external origin.

Moreover, once collected in the third recipient, the portion of midstream urine collected may in the very same container be stored and transported to the analysis laboratory without the necessity for further handling of the urine sample per se by medical personnel. Accordingly, the risk of contamination after collecting the midstream urine sample is considerably reduced.

BRIEF DESCRIPTION OF THE FIGURES

FIG. 4b is an exploded view of the urine collection device illustrated in FIG. 4a.

DETAILED DESCRIPTION OF THE INVENTION

Figure 1A:
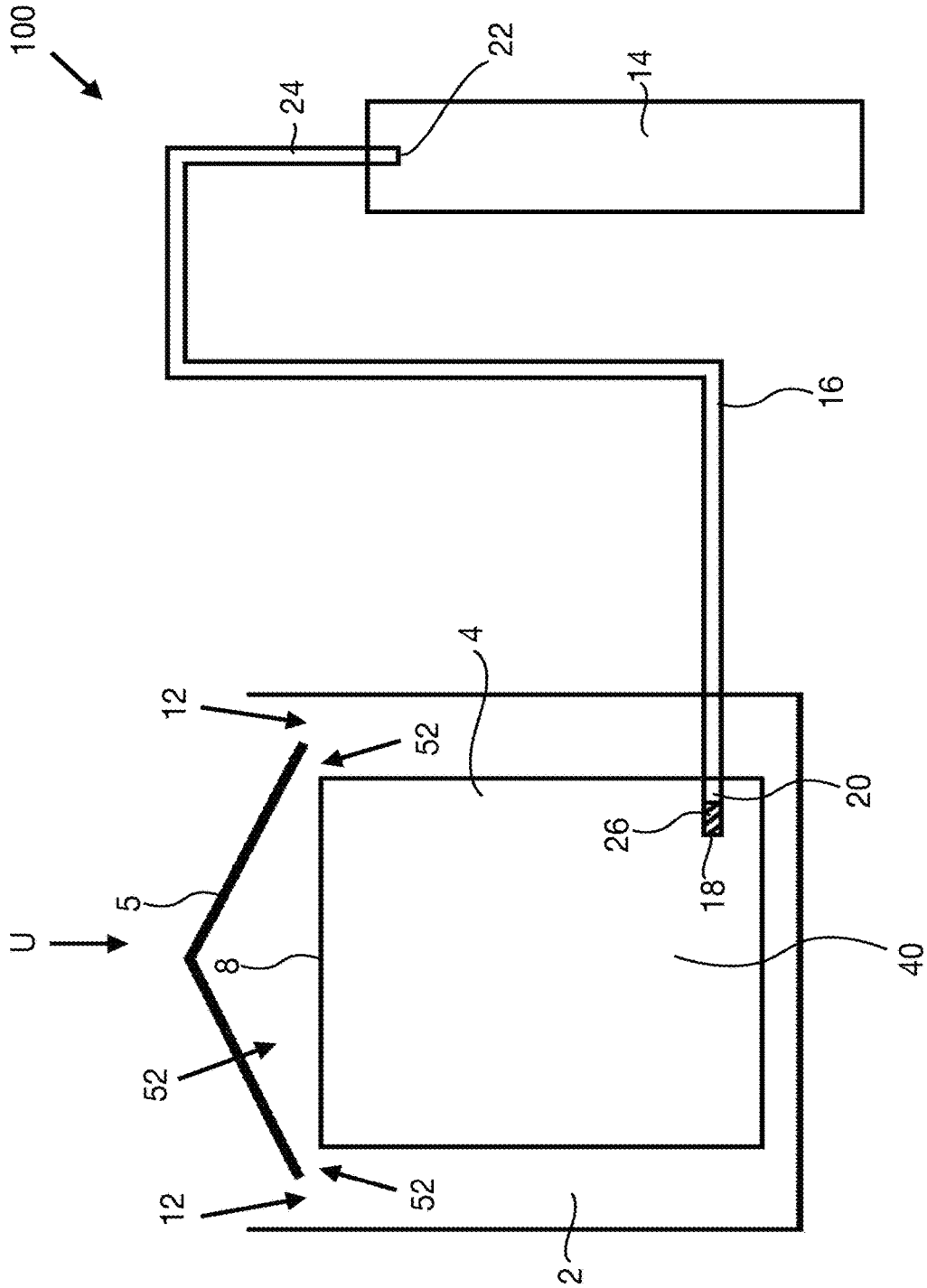
FIG. 1a is principle diagram illustrating the working mode of the urine collection device according to the general first aspect of the present invention.

The First Aspect of the Present Invention

Accordingly, the first aspect of the present invention relates to a urine collection device for collecting midstream urine; wherein said device, in the orientation intended during urine collection, comprising:
a first recipient for urine;
a second recipient for urine;
a urine diverting means;
characterized in that said urine collection device comprises a third recipient for urine, wherein said third recipient for urine comprises an evacuated container; or wherein said third recipient for urine comprises a container which is configured for becoming evacuated by being in fluid connection with a vacuum pump;
wherein said urine collection device comprises a conduit having an opening in a first end and an opening in a second end thereof;
wherein said first end of said conduit is arranged at the interior of said second recipient for urine;
wherein said second end of said conduit is in fluid connection with the interior of said third recipient for urine;
wherein said opening of said first end of said conduit comprises a moist soluble plug, thereby blocking access through said conduit between said second recipient for urine and said third recipient for urine, until dissolution of said plug.

By providing the urine collection device with three recipients for urine as in the design according to the first aspect of the present invention the midstream urine will automatically be separated from a forestream portion of urine and automatically collected in a recipient which is suitable for storing and transportation of the urine sample until analysis thereof.

Thereby any human interference with the midstream portion of urine can be avoided, thus minimizing the risk of external contamination of the midstream sample of urine.

In one embodiment of the urine collection device according to the first aspect of the present invention the urine diverting means is being configured for diverting a first portion of urine being led to the position of said urine diverting means, from above, to enter said first recipient for urine; and is being configured for diverting a subsequent portion of urine being led to the position of said urine diverting means from above, to enter said second recipient for urine.

Hereby a separation of urine into a first stream of urine and a subsequent stream of urine is accomplished.

In one embodiment of the urine collection device according to the first aspect of the present invention the urine diverting means is being positioned at or above an upper opening of said second recipient for urine.

Hereby urine may be separated into a first stream of urine and a subsequent stream of urine when the urine is being suppled to the urine diverting means from above.

In one embodiment of the urine collection device according to the first aspect of the present invention the urine diverting means comprises a moist soluble membrane;

wherein said moist soluble membrane is covering an upper opening of said second recipient for urine;

wherein at least a part of the perimeter of said moist soluble membrane defines an entry into the first recipient for urine.

By providing the urine diverting means as a moist soluble membrane, a first stream of urine provided to said membrane will be diverted to the first recipient for urine, whereas a subsequent stream of urine provided to said membrane will enter the second recipient for urine, as that soluble membrane dissolves by the presence and contact with urine.

In one embodiment of the urine collection device according to the first aspect of the present invention the moist soluble membrane is made from a material independently selected form the group comprising: polyvinyl alcohol, polyvinyl pyrrolidone, alginate, polyacrylamide.

In one embodiment of the urine collection device according to the first aspect of the present invention the urine diverting means comprises a canopy covering an upper opening of said second recipient for urine, thereby preventing urine form entering said second recipient for urine from above, yet allowing subsequent urine to enter said second recipient for urine from below.

In this alternative design of the urine diverting means, a first stream of urine when supplied form above will hit the canopy and be diverted into the first recipient for urine, and as this first recipient for urine becomes filled with urine, a subsequent stream of urine will be able to flow into the second recipient for urine below said canopy and from said first recipient for urine.

In one embodiment of the urine collection device according to the first aspect of the present invention the first recipient for urine at least partly surrounds said second recipient for urine.

Hereby a first stream of urine being led to an area above the urine diverting means will easily be allowed to flow into the first recipient for urine, whereas a subsequent stream of urine will easily be allowed to flow into the second recipient for urine In one embodiment of the urine collection device according to the first aspect of the present invention the one or more essentially vertically arranged baffles, such as 2-24 baffles are arranged between first recipient for urine and said second recipient for urine.

In one embodiment of the urine collection device according to the first aspect of the present invention the device furthermore comprising one or more urine retaining means arranged between said first recipient for urine and said second recipient for urine, preferably along their full circumference, wherein said urine retaining means defines a relative narrow passage for urine between said first recipient for urine and said second recipient for urine, in going from an area above said urine retaining means to an area below said urine retaining means, and vice versa.

By these two embodiments the lower portion of urine (and hence a first portion of urine) being present in the first recipient for urine will be less prone to migrate into the second recipient for urine.

In one embodiment of the urine collection device according to the first aspect of the present invention the upper opening of the second recipient for urine is being arranged below an upper rim of said first recipient for urine.

Hereby, urine will be able to flow from the first recipient for urine into the second recipient for urine.

In one embodiment of the urine collection device according to the first aspect of the present invention the urine holding capacity of said first recipient and/or said second recipient and/or said third recipient independently is comprised within the ranges of 50-250 ml.

These volumes have proven to be sufficient for collection of a sufficient portion of midstream urine.

In one embodiment of the urine collection device according to the first aspect of the present invention the conduit comprises a valve, such as a non-return valve for preventing a flow of urine in a direction from said third recipient for urine to said second recipient for urine.

Hereby it is ensured that midstream, once collected in the third recipient for urine, will not migrate back to the second recipient for urine.

In one embodiment of the urine collection device according to the first aspect of the present invention the interior of said third recipient for urine comprises a vacuum of 600 mm Hg or less, such as 500 mm Hg or less, e.g. 450 mm Hg or less, such as 400 mm Hg or less, e.g. 350 mm Hg or less, such as 300 mm Hg or less, for example 250 mm Hg or less, e.g. 200 mm Hg or less, such as 150 mm Hg or less, for example 100 mm Hg or less, or 50 mm Hg or less.

Accordingly, in order for the urine collection device to work properly, it is not necessary to establish an absolute vacuum or a near absolute vacuum.

Rather, it is a merely a requirement that the vacuum involved is sufficient for transferring, by suction into the third recipient, an amount of urine from the second recipient for urine of approximately 5-15 ml. The above stated magnitudes of evacuation provide for such transfer.

In one embodiment of the urine collection device according to the first aspect of the present invention the first recipient for urine at least partly surrounds said second recipient for urine.

Such a design ensures that the forestream of urine will be diverted into the first recipient for urine, whereas the midstream portion of urine will enter the second recipient for urine.

In one embodiment of the urine collection device according to the first aspect of the present invention the first recipient for urine comprises a urine absorbing material, such as a spongy material or a fibrous material, such as cellulose, such as cotton fiber or paper.

Hereby it can be ensured that a forestream of urine, once collected in the first recipient for urine will not splash around and thereby accidentally enter the second recipient for urine, which is allocated for midstream urine.

In one embodiment of the urine collection device according to the first aspect of the present invention the urine diverting means, when viewed from the outside of said second recipient, and preferably from above, defines a convex cover covering the opening of said second recipient for urine.

Designing the urine diverting means in this configuration will aid in diverting a forestream urine into the first recipient for urine.

In one embodiment of the urine collection device according to the first aspect of the present invention the moist soluble plug is made from a material selected form the group comprising: polyvinyl alcohol, polyvinyl pyrrolidone, alginate, polyacrylamide.

Such materials have proved excellent for the intended purpose of dissolving after exposure for urine for a short period of time.

In one embodiment of the urine collection device according to the first aspect of the present invention the third recipient for urine is a recipient which has previously been sterilized.

Hereby, any contamination, such as bacterial contamination of external origin can be avoided.

In one embodiment of the urine collection device according to the first aspect of the present invention the device further comprises a flow guide for directing urine, flowing or falling by the action of gravity, to an upper part of said first and/or second recipient for urine; wherein the flow guide comprises an upper rim.

Providing the device with a flow guide aids in directing expelled urine from an individual in the vicinity of the area of the first and second recipients for urine.

In one embodiment of the urine collection device according to the first aspect of the present invention the upper rim of said flow guide is provided with an adhesive collar, thereby enabling adhering said urine collection device to the skin of a human individual.

In this embodiment the device can be used by a human individual without the necessity of being combined with a panty or a diaper.

In one embodiment of the urine collection device according to the first aspect of the present invention conduit at least partly comprises a flexible tube.

This will ease the arrangement of the third recipient for urine relative to the second recipient for urine.

In one embodiment of the urine collection device according to the first aspect of the present invention the first end of said conduit is arranged at the interior of said second recipient for urine at a lower portion thereof.

Hereby is assured, that even if only a relatively small amount of midstream urine is collected in the second recipient for urine, this small amount will still be transferred to the third recipient for urine.

In one embodiment of the urine collection device according to the first aspect of the present invention the first recipient for urine comprises a cover partly covering the entry into said first recipient for urine, such as by being provided with one or more openings, such as in the form of one or more holes, perforations or gaps.

Such cover will reduce the tendency of a forestream portion of urine, once collected in the first recipient for urine, to splash around and thereby accidentally enter the second recipient for urine, which is allocated for midstream urine.

In one embodiment of the urine collection device according to the first aspect of the present invention the third recipient for urine comprises an evacuated container.

In one embodiment of the urine collection device according to the first aspect of the present invention the third recipient for urine comprises a container which is configured for becoming evacuated by being in fluid connection with a vacuum pump.

These two embodiments represent alternative ways of ensuring transfer of a midstream portion of urine, collected in the third recipient for urine, into the third recipient for urine.

In one embodiment of the urine collection device according to the first aspect of the present invention the third recipient for urine is made of a transparent or translucent material, thereby allowing visual detection of completion of collection of a midstream portion of urine.

In one embodiment of the urine collection device according to the first aspect of the present invention the device further comprises one or more RFID tags for identification of the identity of the urine collected.

Hereby the risk of mixing up a collected urine sample from one individual for another may be reduced or avoided In one embodiment of the urine collection device according to the first aspect of the present invention the device further comprises one or more sensors, such as movement sensor(s), temperature sensor(s), humidity sensor(s), optionally connected to a transmitter comprised in the device for transmitting data collected by such one or more sensors to a central receiver; said sensor and/or transmitter optionally being in the form of an RFID data logger.

This embodiment allows wireless transfer of data sensed by the sensor to a central receiver. In this way it can be detected when urination of a human individual has taken place.

In one embodiment of the urine collection device according to the first aspect of the present invention the third recipient for urine comprises a leak proof coupling, such as a snap coupling for connecting and disconnecting said conduit.

Such a coupling makes it easy to remove the third recipient for urine, comprising a portion of midstream urine, from the rest of the device, for further processing in the hospital.

In one embodiment of the urine collection device according to the first aspect of the present invention the urine collection device is packed in a sealed package, such as a sterilized, sealed package.

Hereby, any contamination, such as bacterial contamination of external origin can be avoided.

The Second Aspect of the Present Invention

In a second aspect, the present invention relates to a wearable device for collecting urine from a human individual, wherein said wearable device comprises a urine collecting device according to the first aspect of the present invention; wherein said wearable device comprises a material having an inner surface configured to face at least a lower portion of the pelvic region of a human individual, and an outer surface arranged opposite to the inner surface.

Accordingly, the wearable device according to the second aspect of the present invention makes it easy to attach the urine collection device thereof to a human individual.

In one embodiment of the wearable device according to the second aspect of the present invention the wearable device is in the form of a diaper or a panty, such as a disposable panty.

In one embodiment of the wearable device according to the second aspect of the present invention the inner surface comprises a water impermeable lining.

Such lining will aid in directing urine into the vicinity of the first and the second recipient for urine of the urine collection device thereof.

In one embodiment of the wearable device according to the second aspect of the present invention the wearable device, when being worn by a human individual, is configured in such a way that said first recipient and said second recipient of said urine collection device are arranged at a lower portion of said wearable device.

This will ensure that urine, flowing downward by the action of gravity will find its way to the first and the second recipient for urine.

In one embodiment of the wearable device according to the second aspect of the present invention the urine collection device comprises a flow guide as disclosed above in respect of the first aspect of the present invention and wherein said rim of the flow guide is arranged at the inner surface of the wearable device.

In one embodiment of the wearable device according to the second aspect of the present invention the wearable device, when being worn by a human individual, is configured in such a way that said first recipient for urine, said second recipient for urine and said third recipient for urine are arranged opposite to the inner surface of said wearable device.

Hereby room for these recipients are ensured.

In one embodiment of the wearable device according to the second aspect of the present invention the wearable device is packed in a sealed package, such as a sterilized, sealed package.

Hereby, any contamination, such as bacterial contamination of external origin can be avoided.

The Third Aspect of the Present Invention

In a third aspect the present invention relates to a use of the urine collection device according to the first aspect of the present invention, or of a wearable device according to the second aspect of the present invention for collecting a midstream urine from a human individual.

In one embodiment of the use according to the third aspect of the present invention the use does not involve any diagnostic steps per se.

According to this embodiment the use only comprises the steps of collection of midstream urine and not any subsequent analysis or diagnostic steps.

In one embodiment of the wearable device according to the third aspect of the present invention the use involves wearing the urine collection device or the wearable device by a human individual and optionally further involves wearing a standard diaper.

It is preferred that during use, the human individual wearing the device of the first or the second aspect of the present invention, additionally wears a standard diaper on top of the device, in case the device is the urine collection device of the first aspect of the present invention or is a panty according to the second aspect of the present invention.

Referring now to the drawings for better illustrating the present invention in its various aspects, FIG. 1a is a schematic drawing illustrating the principle of the working mode of the urine collection device of the first aspect of the present invention.

FIG. 1a shows a urine collection device 100 for collecting midstream urine.

The urine collection device, in the orientation intended during urine collection, comprises a first recipient for urine, a second recipient for urine and a third recipient for urine.

These recipients for urine are for simplicity represented by the boxes 2, 4 and 14 respectively.

Above the second recipient 4 for urine is arranged a urine diverting means 5.

As explained in more detail below the urine diverting means 5 is being configured for diverting a first portion of urine being led to the position of said urine diverting means 5, from above, to enter the first recipient 2 for urine; and is moreover being configured for diverting a subsequent portion of urine being led to the position of the urine diverting means 5, from above, to enter the second recipient 4 for urine.

Depending on the specific design of the urine diverting means 5, a midstream of urine will either be able to enter the second recipient 4 for urine by passing through the urine diverting means 5, as illustrated by the arrow 52 in FIG. 1a; or alternatively will have to take a detour into the first recipient 2 for urine before entering the second recipient 4 for urine, as illustrated by the combined arrows 12 and 52 in FIG. 1a.

It is seen in FIG. 1a that a conduit 16 having an opening 18 in a first end 20 and an opening 22 in a second end 24 thereof is included in the urine collection device.

The first end 20 of the conduit 16 is arranged at the interior of the second recipient 4 for urine.

The second end 24 of said conduit 16 is arranged at the interior of said third recipient 14 for urine.

In the urine collection device according to the first aspect of the present invention the third recipient 14 for urine comprises an evacuated container, thereby representing a vacuum.

In the opening 18 of the first end 20 of the conduit 16 a moist soluble plug 26 is arranged. This moist soluble plug accordingly blocks access through the conduit between the second recipient 4 for urine and the third recipient 14 for urine, at least until the soluble plug 26 dissolves.

In use the urine collection device 100 is arranged so that a first portion of urine falling or flowing by the action of gravity, as indicated by the arrow U, will, by virtue of the urine diverting means 5, be diverted so as to enter the first recipient for urine 2, whereas a subsequent portion of urine will be allowed, again by virtue of the urine diverting means 5, to enter the second recipient for urine 4. This is described in more detail below.

The stream of urine collected in the second recipient 4 for urine is a delayed portion of urine from the human individual subject to urine collection and this delayed portion of urine represents and qualifies as being a midstream portion of urine which to the extent possible is free of any externally provided bacteria.

When collection of urine in the second recipient 4 for urine has begun, the urine collected therein will start dissolving the moist soluble plug 26 arranged in the opening 18 of the first end of the conduit 16.

Once dissolved, urine collected in the second recipient 4 for urine will, by the action of the vacuum present in the third recipient 14 for urine, be sucked into the third recipient for urine 14.

The third recipient 14 for urine may easily and conveniently be disconnected from the conduit 16 without exposing the urine collected therein for the environment.

Hereby a safe and easy collection of a midstream portion of urine from a human individual is accomplished which moreover excludes risk of external contamination with bacteria.

Figure 1B:
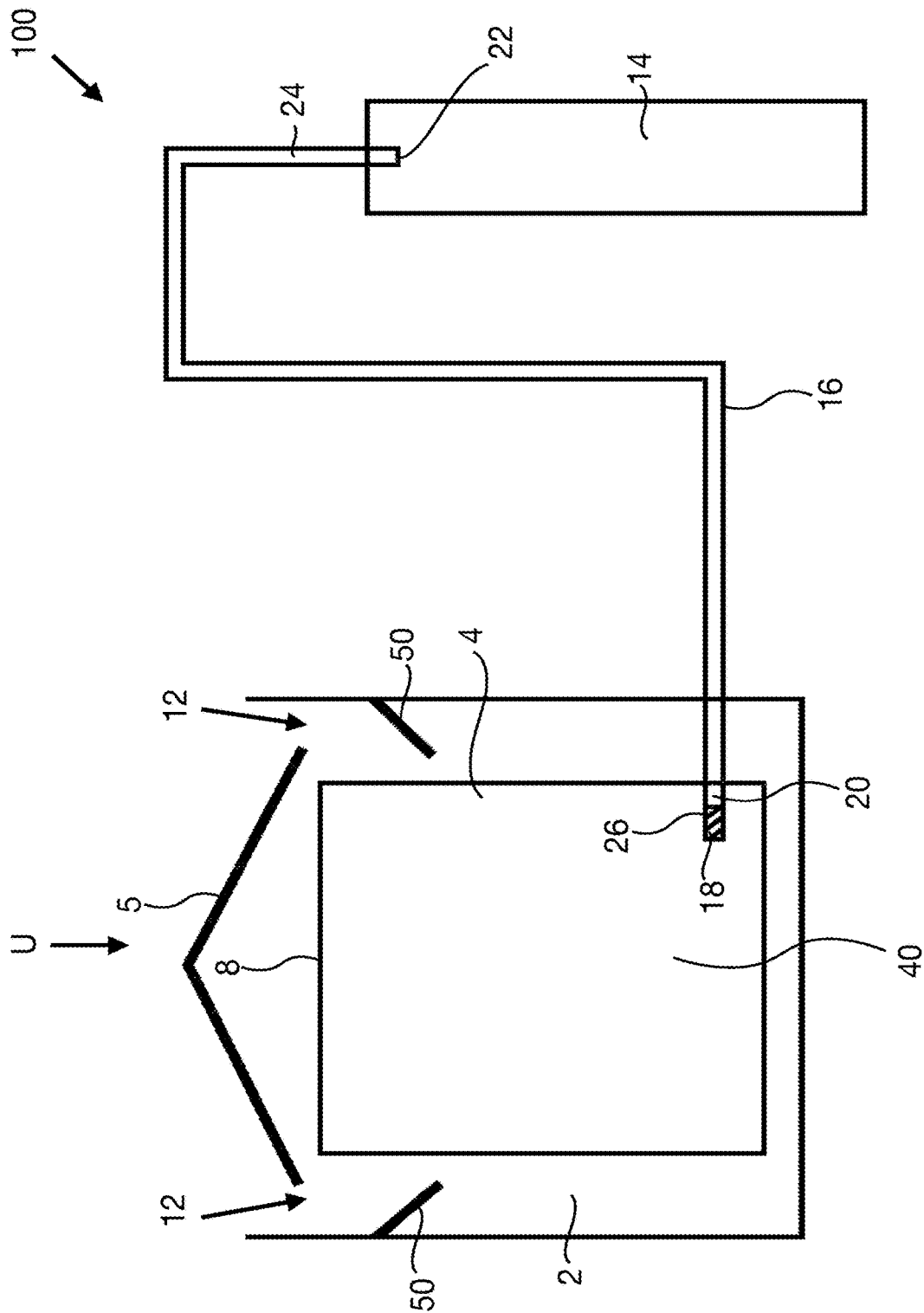
FIG. 1b is principle diagram illustrating the working mode of the urine collection device of FIG. 1a furthermore comprising urine retaining means.

FIG. 1b is a schematic view illustrating the urine collection device of FIG. 1a, wherein the first recipient 2 for urine at least partly surrounds said second recipient 4 for urine, and wherein a urine retaining means 50 has been arranged between the first recipient 2 for urine and the second recipient 4 for urine. The urine retaining means 50 extends along the full circumference of the space between the first recipient 2 for urine and the second recipient 4 for urine. Hereby, the urine retaining means 50 defines a relative narrow passage for urine being present between the first recipient 2 for urine and the second recipient 4 for urine, in going from an area above said urine retaining means 50 to an area below said urine retaining means 50, and vice versa.

This has the consequence that a first stream of urine, upon being collected in the first recipient 2 for urine, will be less prone to enter the second recipient f4 or urine once the level of urine rises in the first recipient 2 for urine.

In other words, as the level of urine rises in the first recipient 2 for urine the urine retaining means 50 aids in preventing urine which has entered the first recipient for urine below the horizontal level of the urine retaining means 50, and hence comprising a first stream of urine, will be less likely to flow to a horizontal level above the urine retaining means 50, whereas a subsequent stream of urine, which enters the first recipient for urine when the level of urine is above the horizontal level of the urine retaining means 50, will be able to flow into the first recipient for urine. Thereby, a mid stream of urine can be collected in the second recipient 4 for urine.

Figure 1C:
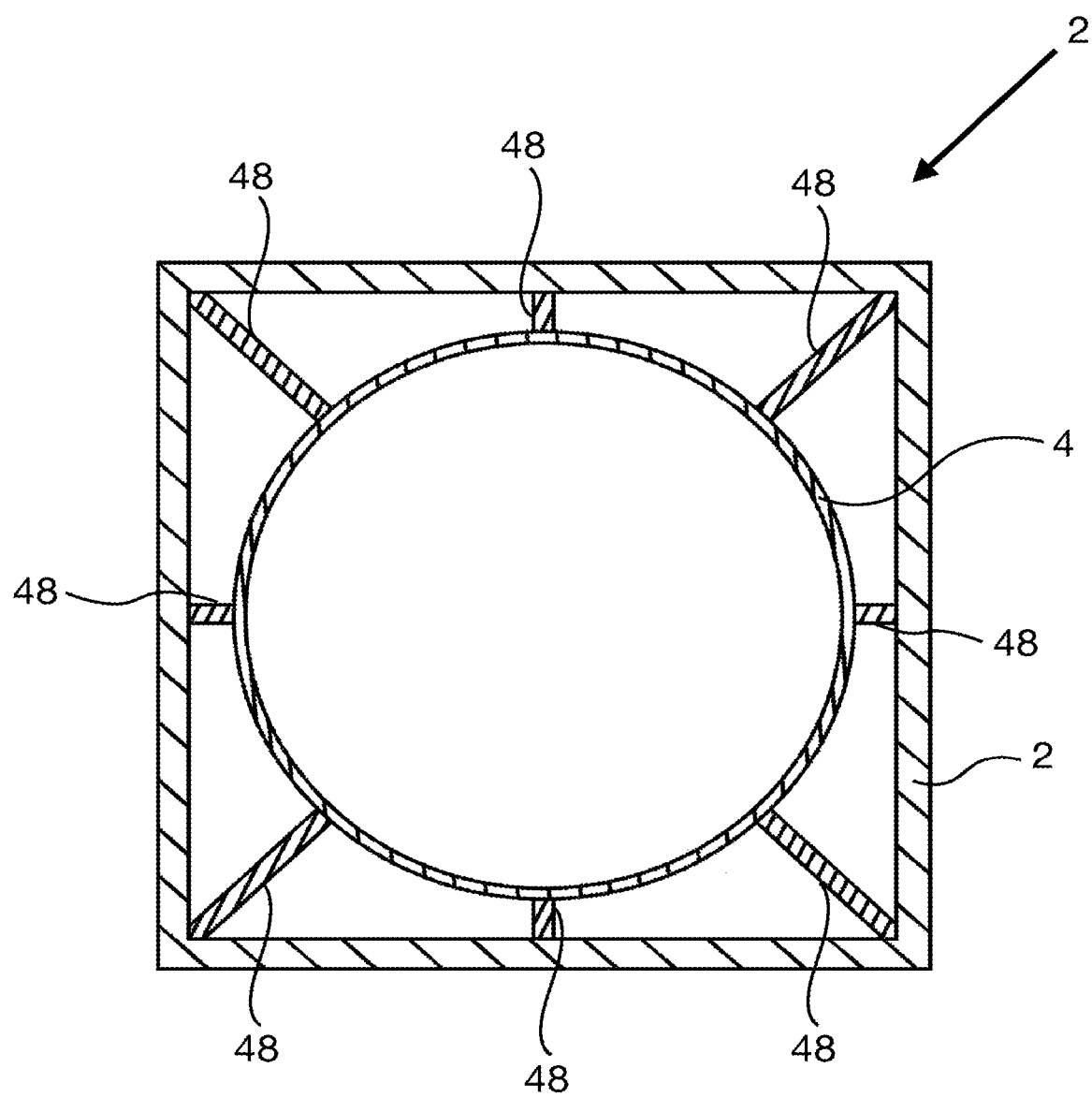
FIG. 1c is a cross-sectional view illustrating the concept of including baffles in the urine collection device.

FIG. 1c is a cross-sectional view illustrating the first recipient for urine 2. It is seen that the second recipient for urine 4 is arranged within the first recipient for urine and that a space thereby is being defined between an inner surface of the first recipient for urine 2 and an outer surface of the second recipient for urine 4.

This space has been provided with a number of baffles 48, which furthermore aids in retaining a first stream of urine in the first recipient 2 for urine, thereby minimizing the amount of a first stream of urine which enters the second recipient 4 for urine.

Figure 1D:
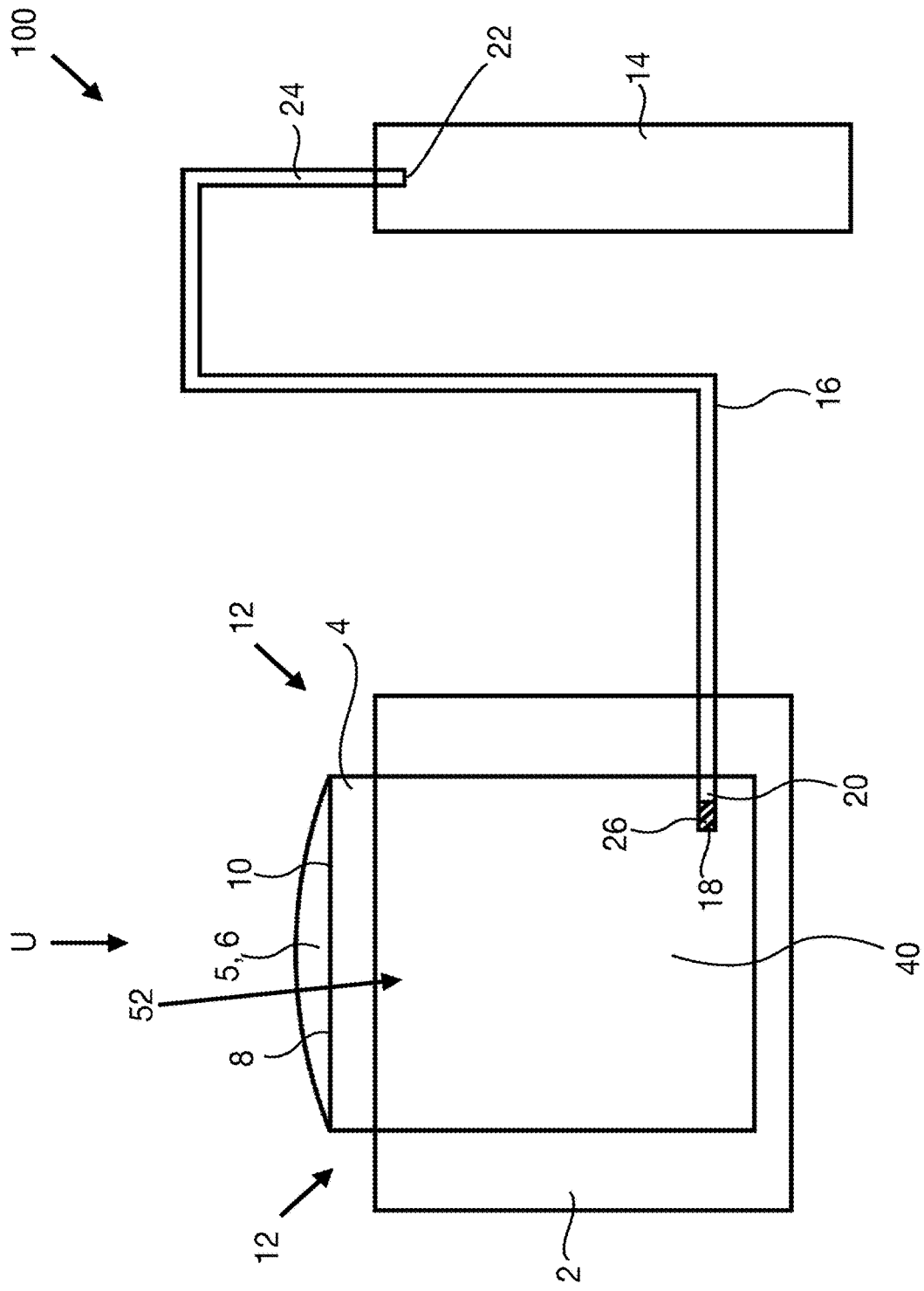
FIG. 1d is principle diagram illustrating one specific embodiment of the urine collection device according to the general first aspect of the present invention.

FIG. 1d is a schematic view illustrating the urine collection device of FIG. 1a, wherein the urine diverting means is in the form of a moist soluble membrane 6 covering an upper opening 8 of the second recipient 4 for urine.

A part of the perimeter 10 of this moist soluble membrane 6 defines an entry 12 into the first recipient 2 for urine.

By virtue of the presence of the moist soluble membrane 6, urine being led to the urine collection device 100 will hit the membrane 6 and be diverted to the entry 12 of the first recipient for urine 2.

However, this complete diversion of urine to the first recipient 2 for urine will only take place as long as the moist soluble membrane 6 remains intact. As the membrane 6 is moist soluble, the moist soluble membrane 6 will eventually dissolve by contact with the urine, whereafter a continued stream of urine will be directed through the opening 8 of the second recipient 4 for urine and into the interior of this recipient.

Figure 1E:
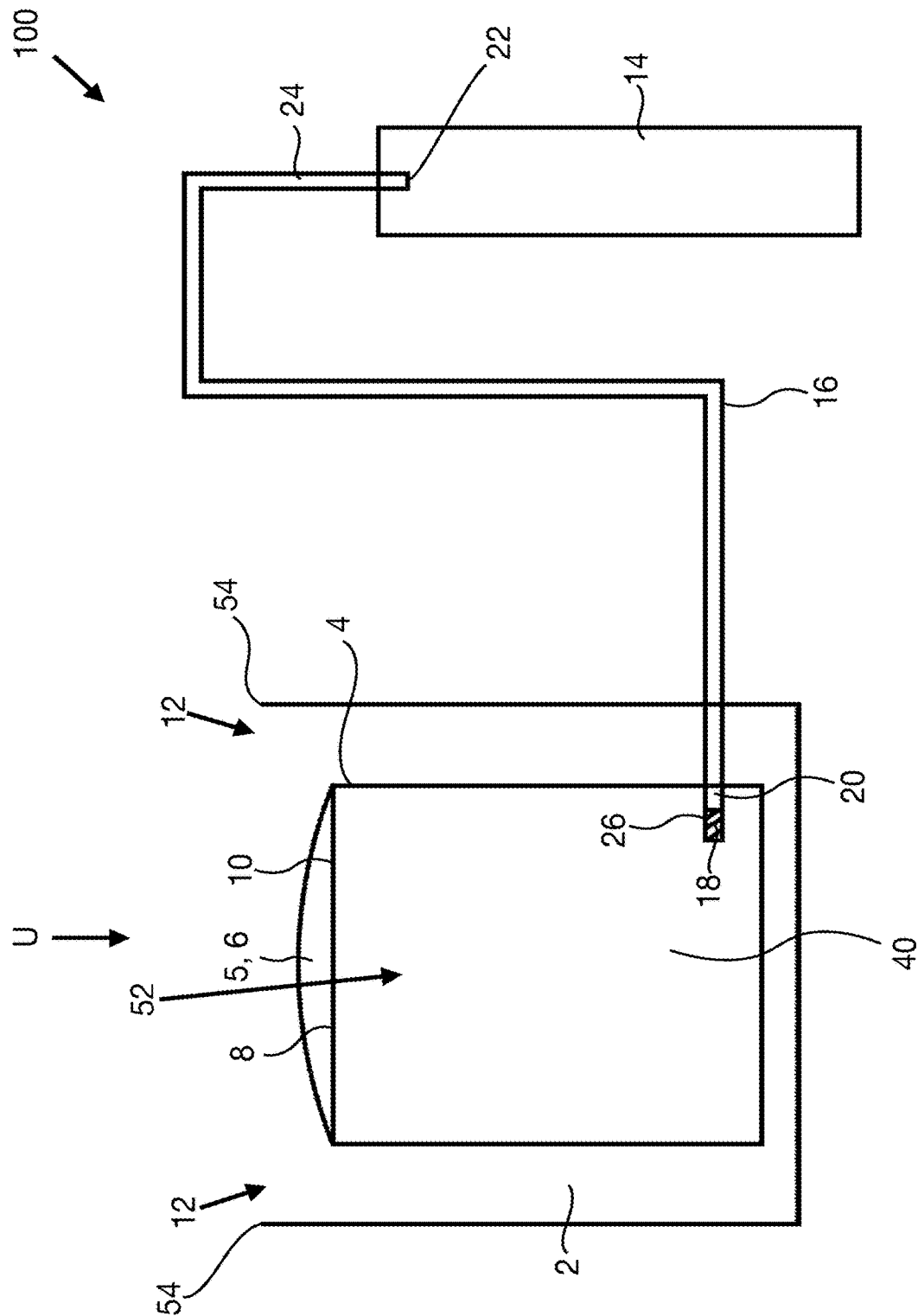
FIG. 1e is principle diagram illustrating a variation of the embodiment illustrated in FIG. 1d.

FIG. 1e illustrates the embodiment of FIG. 1d with the exception that the upper opening 8 of said second recipient 4 for urine is being arranged below an upper rim 54 of the first recipient 2 for urine.

Figure 1F:
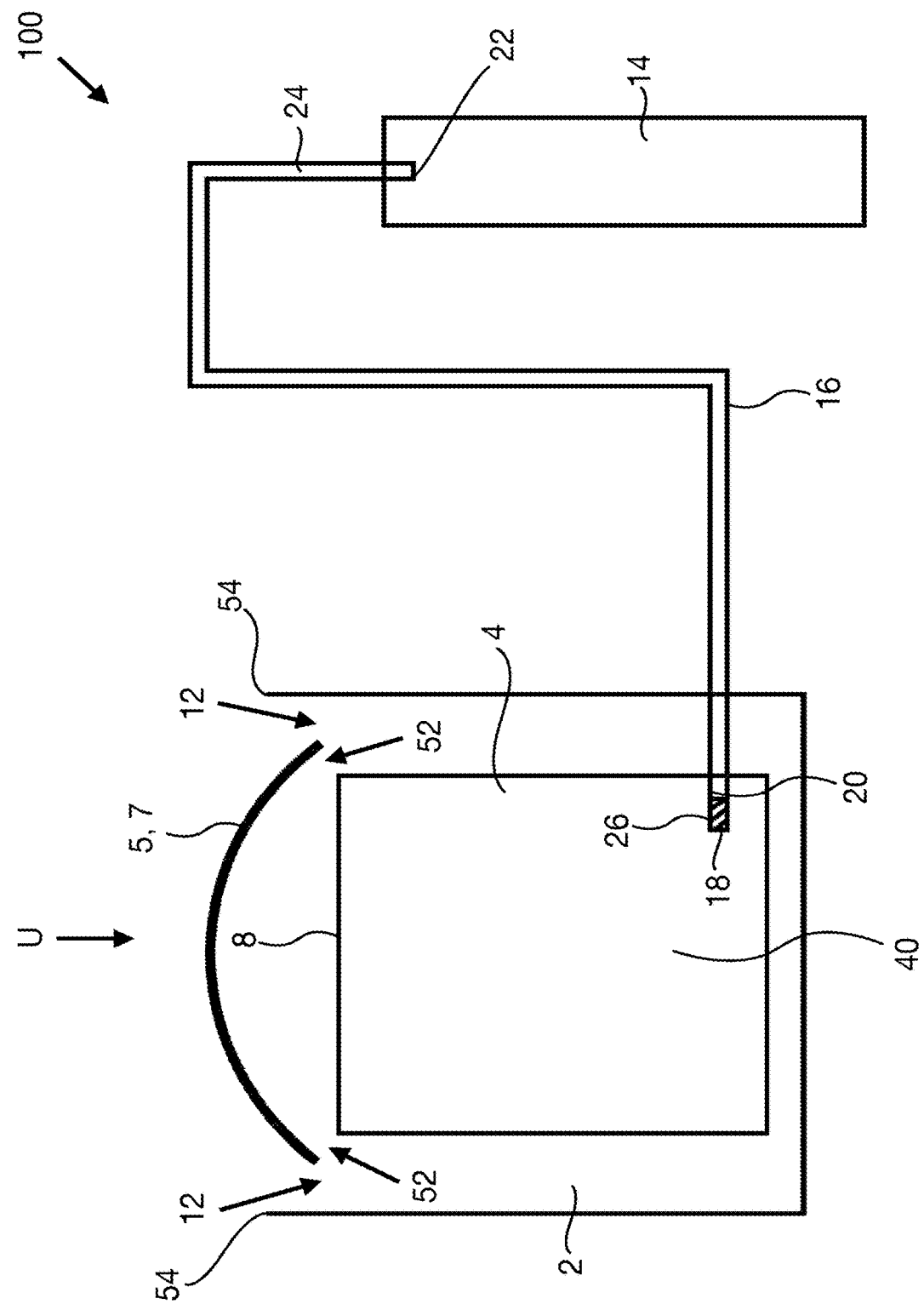
FIG. 1f is principle diagram illustrating another specific embodiment of the urine collection device according to the general first aspect of the present invention.

FIG. 1f is a schematic view illustrating the urine collection device of FIG. 1a wherein the urine diverting means 5 is in the form of a canopy 7.

The canopy 7 is being positioned above an upper opening 8 of the second recipient for urine 4.

Furthermore, the canopy 7 is covering the upper opening 8 of the second recipient 4 for urine, thereby preventing urine form entering said second recipient for urine 4 from above, yet allowing subsequent urine to enter said second recipient for urine 4 from below, as described above with reference to FIG. 1a.

Accordingly, in order for urine to enter the second recipient 2 for urine in the embodiment illustrated in FIG. 1f, urine will first have to flow into the first recipient 2 for urine as illustrated by the arrow 12, as the level of urine rises in the first recipient 2 for urine, a subsequently added portion of urine will be able to follow the arrow 52 and flow into the second recipient 4 for urine.

The first recipient 2 for urine may be in the form of a container as illustrated in FIG. 1. Alternatively, this first recipient 2 may alternatively be in the form of or additionally comprise a urine absorbing material, such as a spongy material.

Figure 2:
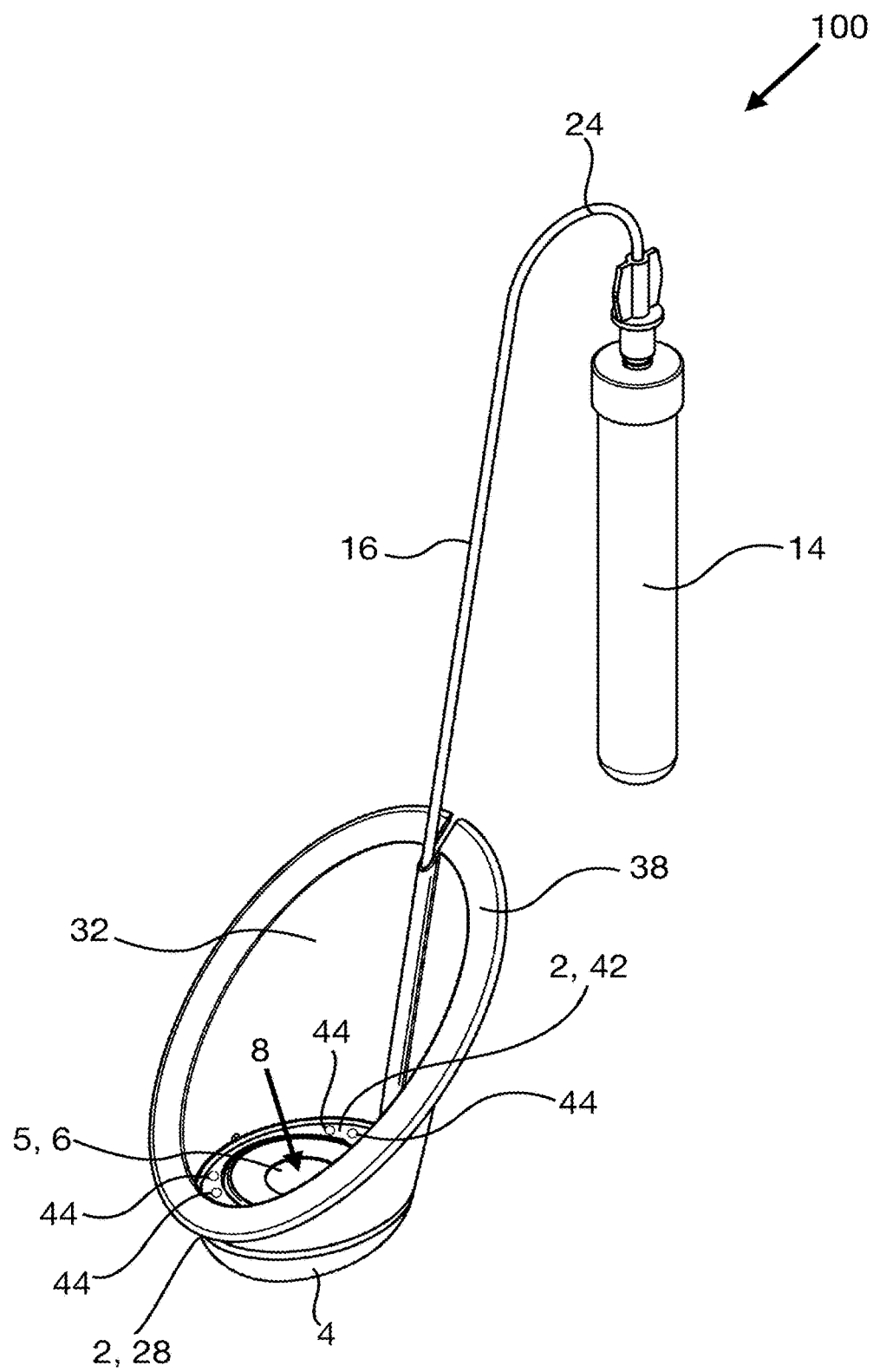
FIG. 2 is a perspective view illustrating an embodiment according the urine collection device according to the first aspect of the present invention.
Figure 3:
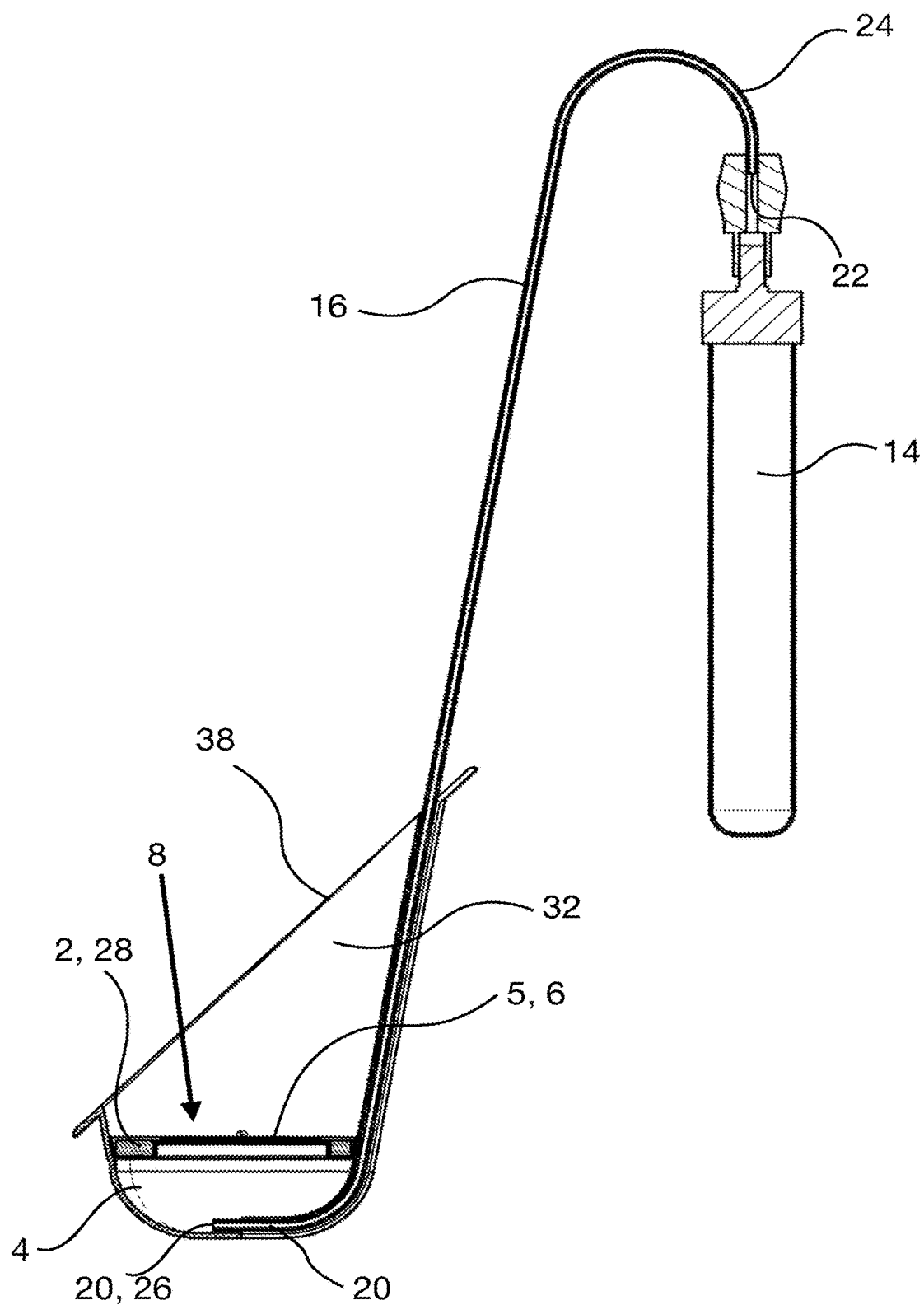
FIG. 3 is a cross-sectional view illustrating the device of FIG. 2.

This is further illustrated in FIGS. 2 and 3.

FIG. 2 is a perspective view illustrating an embodiment according the urine collection device according to the first aspect of the present invention. FIG. 3 is a cross-sectional view of this embodiment. In FIGS. 2 and 3 the urine diverting means 5 is in the form of a moist soluble membrane covering the upper opening of second recipient 4 for urine.

FIGS. 2 and 3 show the device 100 comprising a first recipient 2, a second recipient 4 and a third recipient 14, wherein a conduit 16 in the form of a tube is connecting the interior of the second recipient 4 for urine with the interior of the third recipient 14 for urine.

Again, the second recipient 4 for urine is at an upper opening thereof covered by a moist soluble membrane 5,6, and again the opening 18 in first end 20 of the conduit 16 is provided with a moist soluble plug 26.

In the embodiment illustrated in FIGS. 2 and 3 the first recipient 2 for urine comprises a urine absorbing material 28 in the form of a spongy material or cellulose fibers, such as paper fibers. Accordingly, instead of the situation where a first stream, or forestream, of urine is collected in a container, in the embodiment illustrated in FIGS. 2 and 3 the forestream of urine is merely absorbed by a spongy material 28 surrounding the moist soluble membrane 5, 6 covering the second recipient for urine.

In the embodiment illustrated in FIG. 2 the first recipient 2 for urine comprises a cover 42 comprising a number of perforations 44 therein. The cover 42 is covering an upper opening of the first recipient 2 for urine. Thereby it can be avoided that urine, once collected in the first recipient 2 for urine, subsequently will migrate into the second recipient 4 for urine. Also seen in the embodiment illustrated in FIGS. 2 and 3 is the flow guide 32 comprising an upper rim 38. This flow guide aids in directed a flow of urine to the opening of the upper parts 34 and 36 of the first recipient 2 for urine and the second recipient for urine 4, respectively.

The materials used in the manufacture of the urine collection device 100 according to the first aspect of the present invention may be selected form materials usually employed in the field of urology, such as polyethylene, polypropylene, polyvinyl chloride etc.

Evacuated containers, which have proven suitable for us as the third recipient 14 for urine, in the urine collection device according to the first aspect of the present invention are commercially available. An example of such a commercially available vacuum container is the product "Monovette" manufactured by SARSTEDT.

In an alternative embodiment the third recipient 14 for urine comprises a container which is a non-evacuated container, but is a container, which configured for becoming evacuated by being in fluid connection with a vacuum pump.

Accordingly, in this embodiment, by activating the vacuum pump, either before or after midstream urine has been collected in the second recipient 4 for urine, the midstream portion of urine can be transferred to the third recipient for urine by evacuation of that container.

The embodiment of the urine collection device 100 according to the first aspect of the present invention as illustrated in FIGS. 2 and 3 is suitable for being used in a wearable device. Hereby the invention according to the second aspect of the present invention is attained.

This is further illustrated in FIG. 5 as disclosed below.

Figure 5:
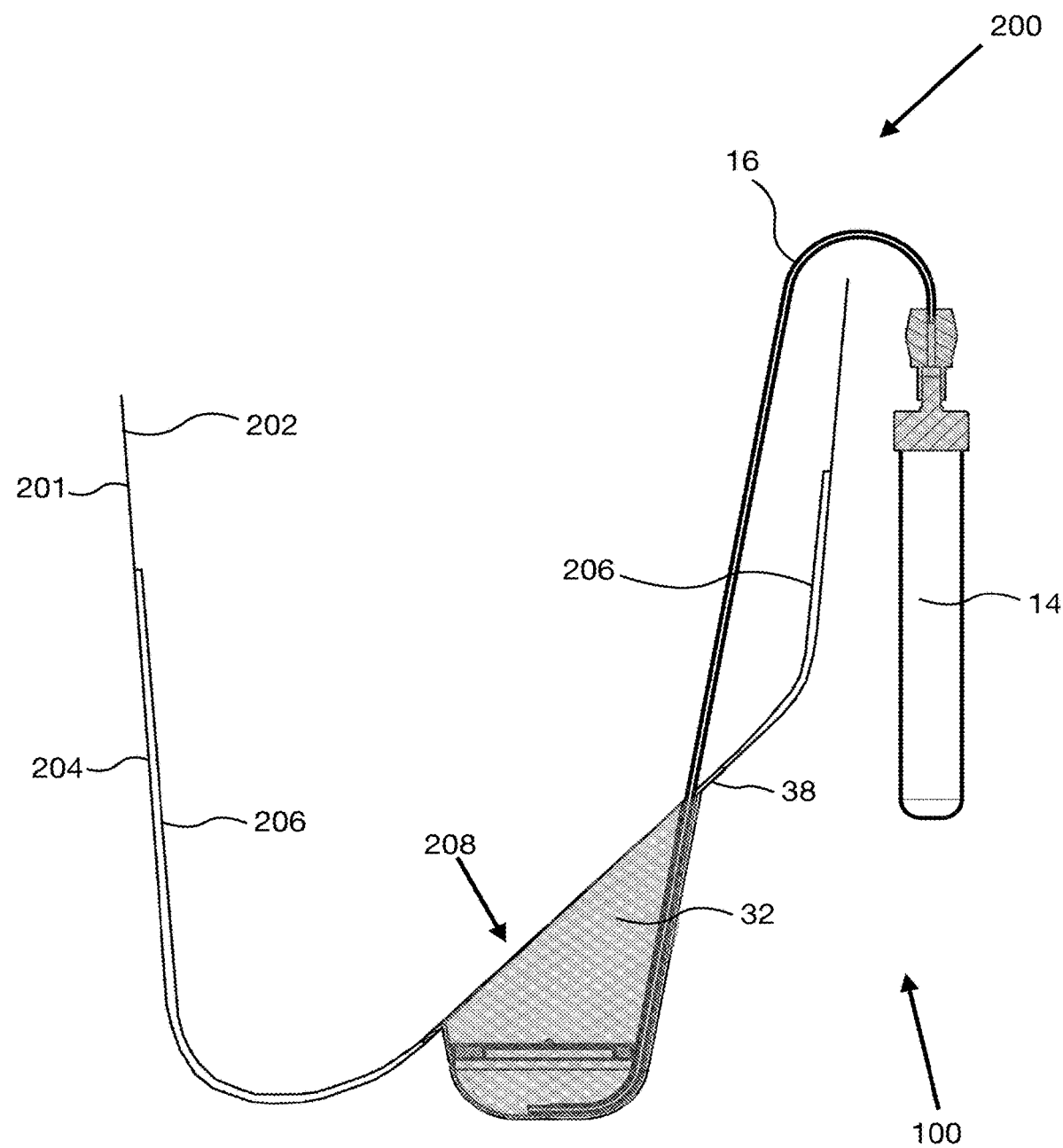
FIG. 5 is an illustration depicting a wearable device according the second aspect of the present invention.

FIG. 5 is an illustration depicting a wearable device according the second aspect of the present invention.

FIG. 5 shows a wearable device 200 for collecting urine from a human individual. The wearable device comprises a urine collecting device 100 according to the first aspect of the present invention. In FIG. 5 the embodiment of the urine collection device corresponds to the device 100 illustrated in FIGS. 2 and 3.

The wearable device 200 illustrated in FIG. 5 comprises a material 201 having an inner surface 202 configured to face a lower portion of the pelvic region of a human individual, and an outer surface 204 arranged opposite to the inner surface.

On the inner surface 202 is arranged a water impermeable lining 206. This lining directs urine to the upper parts 34,36 of the first recipient 2 for urine and the second recipient for urine 4, respectively, thereby leading urine, being present at the inner surface 202 of the material 201 of the device 200, to the urine collection device 100.

As seen in FIG. 5 the upper rim 38 of the flow guide 32 of the urine collection device 100 is attached to a hole 208 in the material 201 in such a way that the flow guide 32 of the urine collection device 100 is arranged at a lower portion of said wearable device and in such a way that that the first recipient 2 for urine, the second recipient 4 for urine and the third recipient 14 for urine are arranged opposite to the inner surface 202 of said wearable device, that is outside the wearable device when being worn by a human individual.

The wearable device may be in the form of a diaper or a panty, such as a disposable panty.

Arranging the third recipient 14 opposite to the inner surface 202 of the material 201 of the wearable device 200 allows for easy detection of delivery of urine from the individual.

Figure 4A:
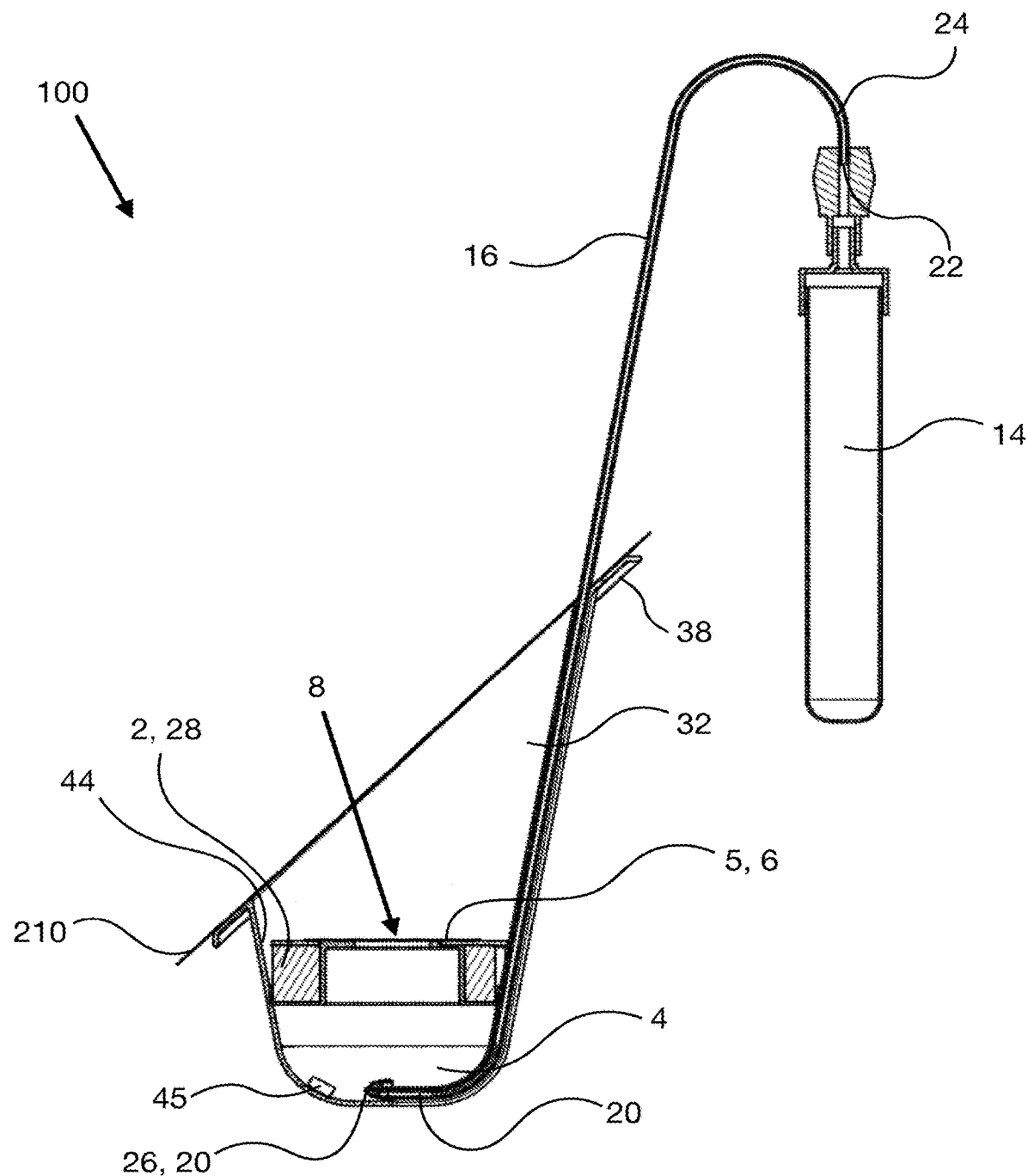
FIG. 4a is a cross-sectional view of an alternative embodiment of the urine collection device illustrated in FIGS. 2 and 3, further comprising an adhesive collar.
Figure 4B:
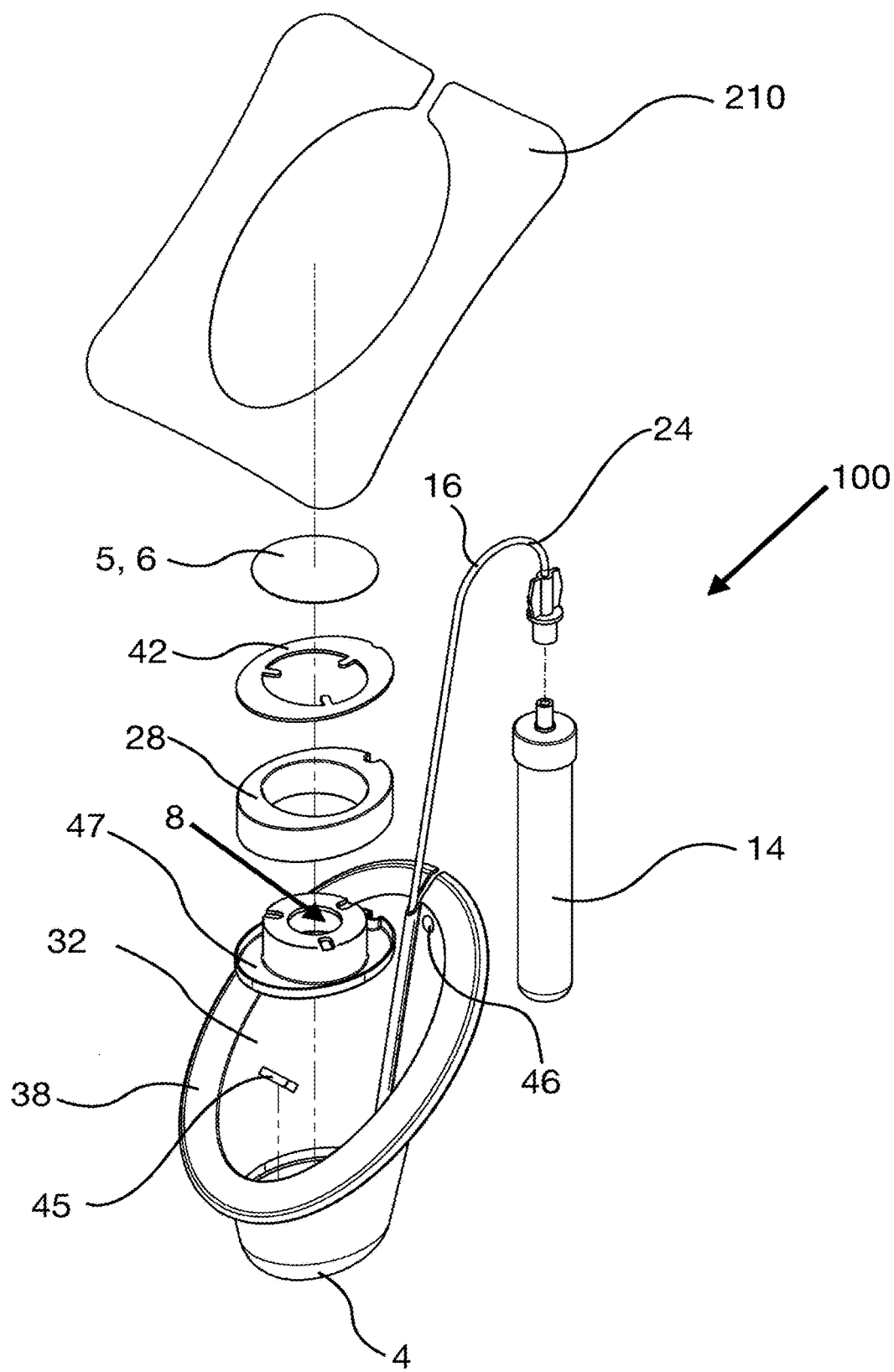

FIG. 4*a* is a cross-sectional view of an alternative embodiment of the urine collection device illustrated in FIGS. 2 and 3. FIG. 4*b* is an exploded view of the urine collection device illustrated in FIG. 4*a*.

FIGS. 4*a* and 4*b* illustrates a urine collection device in essence of similar design as the urine collection device illustrated in the FIGS. 2 and 3.

Accordingly, the urine collection device 100 shown in FIGS. 4*a* and 4*b* comprises a first recipient 2 for urine, a second recipient for urine 4 and a third recipient for urine 14. As in FIGS. 3 and 3 the urine collection device is provided with a flow guide 32 for urine which comprises an upper rim 38.

The upper rim 38 of the flow guide 32 is attached to an adhesive collar 210.

The adhesive is applied to the upper surface of the collar and thereby allows the collar 210 and accordingly the whole device 100 to be adhered to the skin of a human individual, and thereby enclosing the genitals of the individual.

In this way the urine collection device may be worn by a human individual without the necessity of being part of a panty or a diaper.

Also seen in FIGS. 4*a* and 4*b* is that the urine collection device is provided with a combined sensor and transmitter 45. The combined sensor and transmitter is in this embodiment arranged in the second recipient for urine 4 and thereby allows for sensing the appearance of a situation in which urine is being collected in the second recipient 4 for urine. This information may be sent by the transmitter of the combined sensor and transmitter to a central receiver which subsequently will alert hospital personnel that urination by the individual has taken place.

Such combined sensors and transmitters are commercially available under the generic term "sensor tags". The company AMS markets a single chip RFID data logger under the model No. SL900A. This data logger provides for measuring and transmitting a sensed temperature.

The urine collection device 100 illustrated in FIGS. 4*a* and 4*b* also comprises an overflow outlet 46 situated in an upper part of the flow guide 32.

In this way, excessive urine may exit the interior portion of the flow guide and flow through this outlet 46 into a diaper worn by the individual in addition to the device 100.

As it appears from the above sections, the urine collection device 100 when provided with a flow guide 32 and an adhesive collar 210 may be used as a stand-alone device; and alternatively, may be used in combination with a panty, such as a disposable panty or with a diaper.

It should be understood, that all features and achievements discussed above and in the appended claims in relation to one aspect of the present invention and embodiments thereof apply equally well to the other aspects of the present invention and embodiments thereof.

LIST OF REFERENCE NUMERALS

2 First recipient for urine
4 Second recipient for urine
5 Urine diverting means
6 Moist soluble membrane
7 Canopy
8 Upper opening of second recipient for urine
10 Perimeter of moist soluble membrane
12 Entry into first recipient for urine
14 Third recipient for urine
16 Conduit
18 Opening in first end of conduit
20 First end of conduit
22 Opening in second end of conduit
24 Second end of conduit
26 Moist soluble plug
28 Urine absorbing material
32 Flow guide
34 Upper part of first recipient for urine
36 Upper part of second recipient for urine
38 Upper rim of flow guide
40 Lower portion of second recipient for urine
42 Cover of first recipient for urine
44 Opening in entry into first recipient for urine
45 Sensor and transmitter, such as RFID
46 Overflow outlet
47 Support for urine absorbing material
48 Baffle
50 Urine retaining means
52 Access for urine into second recipient for urine
54 Upper rim of first recipient for urine
100 Urine collection device
200 Wearable device
201 Material of wearable device
202 Inner surface of wearable device
204 Outer surface of wearable device
206 Water impermeable lining
208 Hole in material of wearable device
210 Adhesive collar
U Stream of urine

The invention claimed is:

1. A urine collection device for collecting midstream urine, wherein said device, when in an orientation intended during urine collection, comprising:
   a first recipient for urine;
   a second recipient for urine, said second recipient including an interior;
   a urine diverting means;
   a third recipient for urine, wherein said third recipient for urine comprises an evacuated container and an interior; and
   a conduit having an opening in a first end and an opening in a second end thereof,
      wherein said first end of said conduit is arranged at the interior of said second recipient for urine;
      wherein said opening in said second end of said conduit is in fluid communication with the interior of said evacuated container of said third recipient for urine; and
      wherein said opening of said first end of said conduit comprises a moist soluble plug, said moist soluble plug blocking access through said conduit between said second recipient for urine and said evacuated container of said third recipient for urine until dissolution of said moist soluble plug;
      thereby enabling transfer of midstream urine from said second recipient of urine to said third recipient for urine solely upon dissolution of said moist soluble plug by midstream urine being transferred to said second recipient for urine.

2. A urine collection device according to claim 1, wherein:
said urine diverting means is configured for diverting a:
   (i) first portion of urine led to the position of said urine diverting means, from above, to enter said first recipient for urine; and
   (ii) subsequent portion of urine led to the position of said urine diverting means, from above, to enter said second recipient for urine.

3. A urine collection device according to claim 1, wherein:
said second recipient for urine comprises and upper opening; and
said urine diverting means is positioned at or above the upper opening of said second recipient for urine.

4. A urine collection device according to claim 1 wherein:
said urine diverting means comprises a moist soluble membrane;
said second recipient for urine comprises an upper opening; and
   said moist soluble membrane covers the upper opening of said second recipient for urine;
   at least a part of a perimeter of said moist soluble membrane defines an entry into the first recipient for urine; and
   said moist soluble membrane optionally is made from a material selected form the group consisting of polyvinyl alcohol, polyvinyl pyrrolidone, alginate, and polyacrylamide.

5. A urine collection device according to claim 1, wherein:
said second recipient for urine comprises an upper opening; and
said urine diverting means comprises a canopy covering the upper opening of said second recipient for urine, said canopy preventing urine from entering said second recipient for urine from above, allowing subsequent urine to enter said second recipient for urine from below.

6. A urine collection device according to claim 1, wherein the first recipient for urine at least partly surrounds said second recipient for urine.

7. A urine collection device according to claim 6, further comprising:
   one or more vertically arranged baffles arranged between said first recipient for urine and said second recipient for urine.

8. A urine collection device according to claim 6 further comprising:
   one or more urine retaining means arranged between said first recipient for urine and said second recipient for urine, wherein said urine retaining means defines a narrow passage for urine between said first recipient for urine and said second recipient for urine, going from an area above said urine retaining means to an area below said urine retaining means, and vice versa.

9. A urine collection device according to claim 1, wherein the conduit comprises a valve configured to prevent a flow of urine in a direction from said third recipient for urine to said second recipient for urine.

10. A urine collection device according to claim 1, wherein the third recipient for urine comprises a leak proof coupling for connecting and disconnecting said conduit.

11. A urine collection device according to claim 1, wherein said first recipient for urine comprises a urine absorbing material.

12. A urine collection device according to claim 1, wherein said moist soluble plug is made from a material selected form the group consisting of polyvinyl alcohol, polyvinyl pyrrolidone, alginate, and polyacrylamide.

13. A urine collection device according to claim 1, further comprising:
   a flow guide for directing urine, flowing or falling by the action of gravity, to an upper part of said first recipient for urine and/or said second recipient for urine, said flow guide comprising an upper rim.

14. A urine collection device according to claim 13, wherein said upper rim of said flow guide comprises an adhesive collar enabling adhering said urine collection device to the skin of a human individual.

15. A urine collection device according to claim 1, further comprising:
   one or more RFID tags for identification of the identity of the urine collected.

16. A urine collection device according to claim 1, further comprising:
   one or more sensors; and
   a transmitter connected to said one or more sensors, the transmitter for transmitting data collected by said one or more sensors to a central receiver wherein said one or more sensors and/or transmitter optionally being in the form of an RFID data logger.

17. A wearable device for collecting urine from a human individual, said wearable device comprising:
   a urine collecting device according to claim 1; and
   material having an inner surface configured to face at least a lower portion of the pelvic region of a human individual, and an outer surface arranged opposite to the inner surface.

18. A wearable device according to claim 17, wherein the wearable device, when worn by a human individual, is configured in such a way that said first recipient for urine, said second recipient for urine, and said third recipient for urine are arranged opposite to the inner surface of said wearable device.

19. A wearable device according to claim 17 wherein said inner surface comprises a water impermeable lining.

20. A method of collecting urine from a human individual, the method comprising:
 providing a urine collection device according to claim 1; and
 collecting a midstream urine from said human individual with said device.

* * * * *